United States Patent [19]

Mader et al.

[11] 4,146,653
[45] Mar. 27, 1979

[54] PROCESS OF MANUFACTURING DRAGEES

[75] Inventors: Helmut Mader, Furth-Stadeln, Fed. Rep. of Germany; Johann Hopfgartner, Spittal, Drau, Austria

[73] Assignees: J. Pfrimmer & Co., Erlangen, Fed. Rep. of Germany; Arcana Chem.-Pharm. Fabrik Gesellschaft mbH, Spittal, Drau, Austria

[21] Appl. No.: 823,471

[22] Filed: Aug. 10, 1977

[30] Foreign Application Priority Data

Aug. 11, 1976 [DE] Fed. Rep. of Germany ....... 2636152

[51] Int. Cl.² .......................... A61K 9/36; A61K 9/30
[52] U.S. Cl. ........................................ 427/3; 424/31; 424/35; 426/548; 106/162
[58] Field of Search ............... 426/302, 310, 103, 548; 106/162; 424/31, 35; 427/3; 127/29

[56] References Cited

U.S. PATENT DOCUMENTS

| 3,185,626 | 5/1965 | Baker | 427/3 |
| 3,383,237 | 5/1968 | Turech | 424/31 |
| 3,556,814 | 1/1971 | Whitman | 426/310 |
| 3,779,783 | 12/1973 | Bunzer | 424/35 |
| 3,882,228 | 5/1975 | Boncey | 424/31 |
| 3,914,434 | 10/1975 | Bohini | 426/546 |
| 3,991,225 | 11/1976 | Blouen | 427/3 |

OTHER PUBLICATIONS

CA, vol. 71, 11885j, 1969.

*Primary Examiner*—Sam Silverberg
*Attorney, Agent, or Firm*—Karl W. Flocks

[57] ABSTRACT

A dense dragee surface layer is provided by coating the dragee at 85°–90° C. with a melt of xylitol and sorbitol in a weight ratio of 9:1 to 1:1.

5 Claims, No Drawings

PROCESS OF MANUFACTURING DRAGEES

FIELD OF INVENTION

The present invention relates to pharmaceutical preparations, and, more particularly, to a method of making dragees.

BACKGROUND OF THE INVENTION

Dragees represent oral application forms of medicaments, i.e. cores obtained in any manner containing in suitable quantities the medicaments or pharmaceuticals, and provided with a coating, i.e. the dragee casing. Such coating can be used for various purposes. The surface of the dragee should thus be made smooth, so that it can be readily swallowed in which connection any unpleasant taste inherent in the medicament should possibly be masked. Further, the coating should improve the appearance of the dragee, distinguish it by means of color and, in many cases, exert an effect on the breaking up of the dragee core in the gastrointestinal tract, in particular retard the dissolving of the effective substances.

Such dragee coatings are often made especially of sugar composition which may contain dye and pigment additives, as well as film-forming agents. The coatings are applied from solutions in aqueous or organic solvents often in several layers by spraying such solutions, possibly in connection with the simultaneous addition of further pulverulent coating materials, on the tablets or dragee cores arranged in a rotating dragee-container or a fluidized-bed device, while blowing in warm air. As film-forming agents, there may be employed generally shellac, cellulose derivatives, such as cellulose acetate phthalate, as well as possibly substituted polymers of acrylic or methacrylic acid, in which connection such film-forming agents should provide some resistance to gastric juice and retard the release of the active substances.

The coating must provide an optimal seal in the case of unpleasantly tasting and strongly smelling active agents. The film-forming materials based on high-molecular substances which could as such provide a good seal, lead to a delay in the breaking up of the dragee, which is frequently undesirable. The use of such film-forming agents for the coating also represents an undesirable burdening of the patient, in particular in the case of such unpleasantly tasting or smelling medicaments, that must be taken in considerable amounts by patients and are thus applied generally in the form of microdragees, that can be swallowed more readily in large numbers and possess a diameter of 0.4–4mm, preferably at most 1.5–2mm. Such burdening of the patient takes place especially because the percentage of the film-forming polymers is relatively large in comparison with the active agent in the case of microdragees.

Although microdragees are particularly suitable for administering large amounts of badly tasting or smelling medicaments, such as essential amino acids or their keto and hydroxy analogs that must be dosed, e.g. in the amounts of about 15 to 20g per day in the case of uremia patients, no satisfactory industrial method of manufacture was possible until the present time. The solution of the problem failed especially on the fact that the processes and coating means known until the present for masking the taste and smell either exhibit unsatisfactory effects during the dragee-making or there are required excessive amounts of such coating materials, that are not desired as such, but must then be administered to the patient together with the active materials. Reactions may also take place between the coatings and the medicaments, that are frequently reactive and unpleasantly tasting and smelling, which reactions may occur during the manufacture of the dragees through the action of high temperature of drying or which result from the use of organic or aqueous solutions; such reactions may also introduce moisture and decomposition, which later comprise microbial decay. Coatings consisting of fat can be penetrated by lipophilic substances and can thus be used only to a limited extent.

SUMMARY

Unexpectedly, it has now been found that improved dragees for peroral administration of medicaments, in particular those of bad taste and smell, can be obtained by using in accordance with the invention a fusion product (or melt) of xylitol and sorbitol for the application of the coating. Preferably, there is used a fused mixture of xylitol and sorbitol in the quantitative ratio of 9:1 to 1:1. The prior problems appearing in connection with dragees, especially microdragees, such as those indicated above are ideally solved through the use of such sugar-alcohol fusion in place of the coating solutions heretofore used, in which connection one has then available physiologically unobjectionalbe or even physiologically valuable substances as coating compositions and comprising xylitol and sorbitol.

The sugar alcohols xylitol and sorbitol are distinguished by their great chemical stability and indifference, i.e., inertness, so that the two can be used for encasing a great variety of badly tasting and smelling cores of medicaments. In the case of the combination, the mixture possesses a melting point, which is clearly situated below 100° C. The sugar-alcohol fusion or melt rapidly solidifies into a dense glass-like mass, which is distinguished through a pleasantly sweet and fresh taste of its own. The novel coating is capable of binding and compensating the bad smelling and tasting substance even in large amounts. Accordingly, the invention relates to a process of manufacturing dragees for peroral administration of medicaments by coating the medicament-containing dragee cores with a dense coating, characterized in that the dragee cores are coated with a melt of xylitol and sorbitol at 85°–90° C.

DETAILED DESCRIPTION OF EMBODIMENTS

The great water-binding capacity of the coating consisting of the two sugar alcohols has turned out as a further advantage, so that the dragee cores thus coated possess an almost unchanged content of water through a long period of time even at high air moisture. The reduced permeability to oxygen is also of advantage in relation to the dragee coatings produced by standard methods. This is all the more unexpected, since the two sugar alcohols can be used only unsatisfactorily as dragee-making agents in the known dragee-making processes. For example, if xylitol or sorbitol is sprayed on the cores, e.g., in the form of a 50 or 60% aqueous solution, as previously customary for sugar solutions, one obtains brittle, cracked and irregular formations having a low durability.

The process of the invention represents an elegant economical method of manufacturing dragees, in particular microdragees, since sorbitol and/or xylitol, preferably as a mixture in the indicated quantitative ratio, especially in a ratio of 72% by weight xylitol and 28% by weight sorbitol, are mixed and heated and the melt is applied to the cores as a coating. At the preferred mixture ratio of about 7.2:2.8 the melting temperature is only about 85° C. It is clearly lower than the melting points of the two polyols separately (melting point of xylitol is 95° C.; and that of sorbitol 111° C.), so that in comparison with the use of the separate sugar alcohols, the mixture possesses advantages especially in connection with heat-sensitive medicaments.

The application of the melt at a temperature of about 85° C. on the microdragee cores of pellets, pre-manufactured in known manner and containing the active ingredients, can be effected by means of devices ordinarily used for such purposes at the present time, e.g., in a dragee container, preferably by means of an immersion or spray tube, which is surrounded by a flow of rotating cores or pellets. In order to secure a satisfactory structure of the dragee casing, one must control merely the rate of spraying. The blowing-in of warm air, drying with infrared lamps, cooling or similar measures can be omitted here, since the melt solidifies rapidly and the dragees are dry immediately after coating, so that the removal can be effected at a hardly increased temperature. A particularly good coating is obtained when up to 5% of water and about 0.01–0.02% polyglycol is added to the poly melt; these additives somewhat retard the rate of solidification and one thus obtains an even more homogeneous smooth surface together with particularly firm adherence to the core.

At the temperature required for keeping the sugar alcohols in the fused state, the viscosity is sufficiently low for securing a rapid distribution of the fused mixture of substances on the core surface during the spraying. The cooling on the core then produces a rapid increase in viscosity and solidification of the coating material, so that a uniform microcrystalline layer in the form of the solidified polyol mixture is formed. This brings about the great uniformity of the coating as well as the excellent density and durability of the dragee casing.

In addition to the possibility of full automation, further advantages of the novel process consist in the relatively short treatment period and the elimination of the additional steps, such as drying, smoothing and polishing. Because of their inertness, xylitol and sorbitol can be kept for days at the temperature of melting without noticeable change. In contrast with this, in the case of fusing the standard carbohydrates, such as saccharose, there would occur a conversion into caramel and, finally, decomposition.

The microdragees produced in accordance with the invention with the sugar alcohols sorbitol and xylitol and having a diameter of up to 4mm are characterized during rise thereof, in that their osmotic effect is unfolded immediately, due to their capacity of immediately beginning to dissolve, so that a sufficient amount of saliva is soon formed in the mouth, which makes it possible to swallow the form of administration without an additional liquid. For the administration of large amounts of active ingredients which must be dissolved in the stomach, for example, because the salts are insoluble in water (e.g., calcium salts of the α-keto acids), such ingredients must be dissolved by the gastric acids and in such case the form of administration provided by the present invention is particularly ideal, because the microdragees coated in accordance with the invention break apart within 5 minutes in the stomach. On the other hand, dragees manufactured in standard fashion generally possess a breaking-up time of about 60 minutes. For many patients taking daily about 15–20g active ingredient ≙ about 20–50 dragees, such long breaking-up time represents an additional burdening of the stomach and, beyond that, it renders more difficult rapid biological availability to the patient, it being understood that such availability must be as quantitative as possible.

Medicaments, such as keto or hydroxy analogs of amino acids, that possess a particularly unpleasant taste, can now be coated without problems in the form of granulates or pellets. In contrast with what occurs when there is used fat-consisting coating materials, these fat-soluble active compounds do not diffuse through the dragee casings of the invention even when stored for long periods of time. Also, amino or keto compounds, for example, do not react with the sugar alcohols, which is in contrast with the conventional sugar or starch-containing coating materials.

The encasement with the sugar alcohols xylitol and sorbitol makes the taking of dragees possible also for diabetics, since such carbohydrates can be utilized in the organism independently of insulin. The greater the amount of dragees to be administered, the more important is this advantage. At relatively large amounts of medicaments to be taken during the entire day, the caries-promoting effect of the carbohydrates heretofore used represents an additional disadvantage of considerable importance. The coating of xylitol and sorbitol in accordance with the present invention prevents or at least reduces the risk of caries disease from this point of view.

It is obvious for the man of the art that the form or shape of dragees does not restrict the invention, nor does the nature of the active ingredients.

The medicaments to be made into dragees can either be in the form of flat or convex tablet blanks, round pills or in the form of small compressed elements, e.g., pellets, spray granulates or the like, and then provided with the dragee coating of the present invention.

The following examples are employed for explaining the process and should in no way indicate a restriction of the applicability of the invention.

EXAMPLE 1

1700g α-keto acids is applied by means of the customary adhesive solutions, e.g., PVP or gum arabic on a 0.4–0.5mm core through spraying. The air-dried pellets are then coated in a dragee container or kettle by means of a spray tube with a melt consisting of 1728g xylitol and 672g sorbitol.

EXAMPLE 2

900g of essential amino acids are processed into pellets as in example 1 and then coated with a melt consisting of 720g xylitol and 480g sorbitol.

EXAMPLE 3

1400g α-keto acids and 250g essential amino acids are processed into pellets as in example 1 and then coated with a melt consisting of 1040g xylitol, 260g sorbitol, 60g water and 0.15g polyglycol.

EXAMPLE 4

1700g spherical microcompressed elements of amino acids, inorganic components and vitamins is coated with a melt of 1440g xylitol, 560g sorbitol and 100g water.

EXAMPLE 5

580g α-hydroxy acid is processed into pellets as in example 1, which pellets are then coated with 420g of a xylitol melt.

In every example it is still possible to add dyes and aromatic materials to the melt and spray such dyes and materials together with the melt.

It will be obvious to those skilled in the art that various changes may be made without departing from the scope of the invention and the invention is not to be considered limited to what is described in the specification.

What is claimed is:

1. In a process of manufacturing dragees for peroral administration of medicaments, by coating the medicament-containing dragee cores with a dense coating, the improvement wherein the dragee cores are coated at a temperature at about 80°–90° C. with a melt consisting essentially of a mixture of xylitol and sorbitol.

2. A process as in claim 1, wherein there is used a mixture of xylitol and sorbitol in a weight ratio of 9:1 to 1:1.

3. A process as in claim 2, wherein the melt of xylitol and sorbitol contains up to 5% water and up to 0.5% polyglycol.

4. A process as in claim 1 for manufacturing microdragee cores containing α-keto acids, α-hydroxy acids, amino acids or mixture thereof.

5. A process as in claim 2 wherein said mixture comprises 7.2 parts of xylitol per 2.8 parts of sorbitol.

* * * * *